(12) United States Patent
Linder

(10) Patent No.: US 10,668,056 B2
(45) Date of Patent: Jun. 2, 2020

(54) PHARMACEUTICAL COMPOSITION COMPRISING INDOLE DERIVATIVES, PROCESS FOR PREPARATION AND USE THEREOF

(71) Applicant: VIVOLUX AB, Uppsala (SE)

(72) Inventor: Stig Linder, Bromma (SE)

(73) Assignee: VIVOLUX AB, Uppsala (SE)

( * ) Notice: Subject to any disclaimer, the term of this patent is extended or adjusted under 35 U.S.C. 154(b) by 0 days.

(21) Appl. No.: 16/061,868

(22) PCT Filed: Dec. 10, 2016

(86) PCT No.: PCT/EP2016/025175
§ 371 (c)(1),
(2) Date: Jun. 13, 2018

(87) PCT Pub. No.: WO2017/102097
PCT Pub. Date: Jun. 22, 2017

(65) Prior Publication Data
US 2018/0280366 A1 Oct. 4, 2018

(30) Foreign Application Priority Data
Dec. 18, 2015 (SE) ..................... 1500520

(51) Int. Cl.
| | | |
|---|---|---|
| *C07D 471/04* | (2006.01) | |
| *A61K 31/444* | (2006.01) | |
| *A61P 35/00* | (2006.01) | |
| *A61K 9/19* | (2006.01) | |
| *A61K 9/00* | (2006.01) | |

(52) U.S. Cl.
CPC .............. *A61K 31/444* (2013.01); *A61K 9/19* (2013.01); *A61P 35/00* (2018.01); *C07D 471/04* (2013.01); *A61K 9/0019* (2013.01)

(58) Field of Classification Search
CPC .................................................. C07D 471/04
See application file for complete search history.

(56) References Cited

U.S. PATENT DOCUMENTS

2003/0092716 A1* 5/2003 Almstead ............. A61K 31/135
514/247

FOREIGN PATENT DOCUMENTS

| WO | WO 2009/035534 A2 * | 3/2009 |
|---|---|---|
| WO | WO 2012/128689 A1 | 9/2012 |
| WO | WO 2014/046589 A1 | 3/2014 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Eshba N H et al: "Synthesis of some substituted 1,2,4-triazino[5,6-b]indole derivatives as potential antiviral and anticancer agents", Die Pharmazie: An International Journal of Pharmaceutical Sciences, Govi Verlag Pharmazeutischer Verlag GMBH, DE, vol. 42, No. 10, Jan. 1, 1987 (Jan. 1, 1987), pp. 664-666, XP009029588.
Xiaonan Zhang et al: "Induction of mitochondrial dysfunction as a strategy for targeting tumour cells in metabolically compromised microenvironments", Nature Communications, vol. 5, Feb. 18, 2014 (Feb. 18, 2014), XP055264964.

* cited by examiner

*Primary Examiner* — Shawquia Jackson
(74) *Attorney, Agent, or Firm* — Polsinelli PC

(57) ABSTRACT

The invention provides well-defined and stable pharmaceutical compositions comprising indole derivatives of general formula 1, a process for the preparation of di-hydrochloride salts comprising a high content of the pharmacologically active isomer suitable for industrial production, and use of these in pharmaceutical compositions. The invention further provides a method for use of said compounds for the treatment of cancer. The invention also provides methods to use these compounds in conjunction with other therapies commonly used for treating cancer diseases.

Formula 1

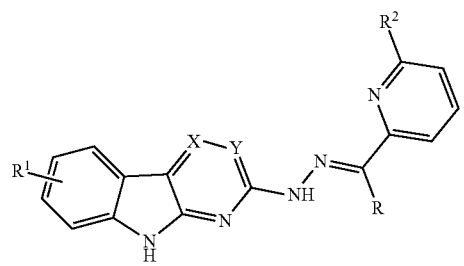

15 Claims, 4 Drawing Sheets

A (FIG. 4 CONTINUED)
B
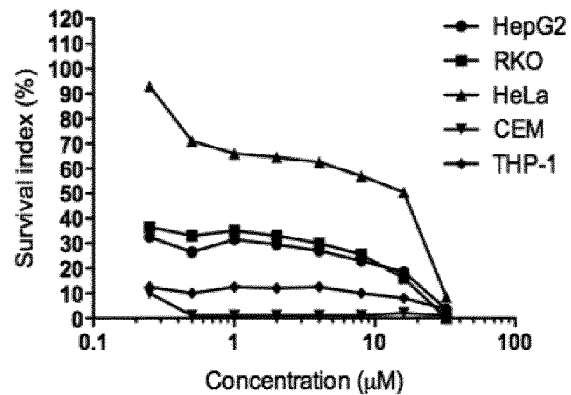
(FIG. 4 CONTINUED)
C
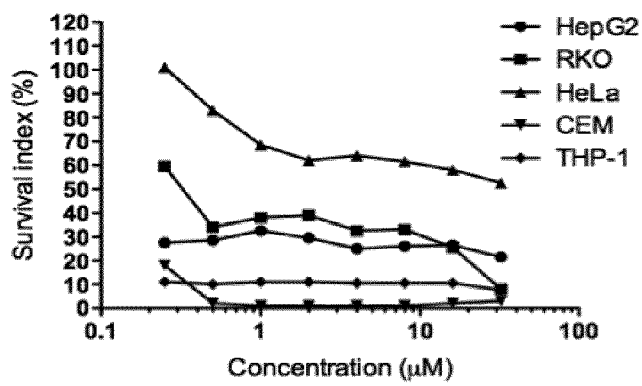
(FIG. 4 CONTINUED)
D
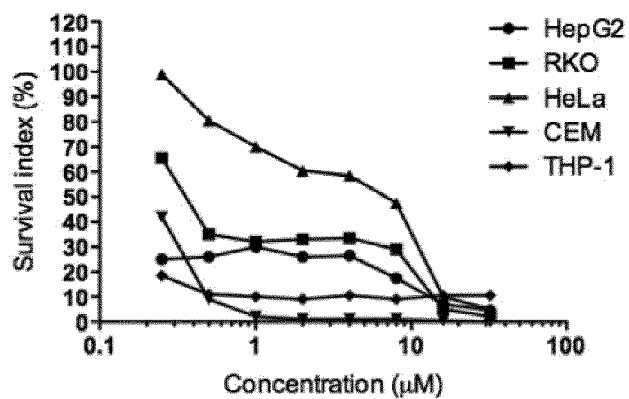

PHARMACEUTICAL COMPOSITION COMPRISING INDOLE DERIVATIVES, PROCESS FOR PREPARATION AND USE THEREOF

CROSS REFERENCE TO RELATED APPLICATIONS

This application is the National Phase of Application No. PCT/EP2016/025175 filed Dec. 10, 2016, which claims priority to Application No. 1500520-0 filed in Sweden on Dec. 18, 2015 under 35 U.S.C. § 119. The entire contents of each application are hereby incorporated by reference.

FIELD OF THE INVENTION

The present invention relates to an improved and stable pharmaceutical composition of indole derivatives, comprising a high content of the pharmacologically active isomer thereof. The present invention also relates to a method for the treatment of cancer by use of the compositions and to a process for its preparation. The invention further relates to enabling large scale synthesis of the pharmacologically active compounds.

BACKGROUND OF THE INVENTION

Indole derivatives and pharmaceutically acceptable salts thereof are disclosed in WO 2012/128689 and WO 2014/046589 in form of mixtures of cis/trans isomers (Z/E isomers) at the N-methylidene entity. These compounds are useful in the treatment of solid cancers. The anti-cancer effect is believed to be based on the iron-chelating property of the compounds. Since the rate of isomerization at physiological conditions seemed to be substantial it was presumed that the pharmacological effect of the isomers was substantially similar or even the same.

Eshba et al., discloses N-(1-pyridine-2-yl-methylidene)-N-(9H-1,3,4,9-tetraza-fluoren-2-yl)-hydrazine derivatives as antiviral and anti-cancer agents, wherein only one compound show cytotoxic activity. It is desirable for a pharmaceutical composition to be well-defined, in particular of its pharmacologically active constituents. It is therefore essential that if a compound exists in two isoforms, the more active isomer of said compounds has to be dominant in the pharmaceutical composition thereof. In addition, a pharmaceutical composition should be sufficiently stable allowing it to be stored for an extended period of time without noticeable change of its constitution.

New and effective anticancer drugs need to be developed for patients that suffer from cancer. Drug development over all is associated with a lot of difficulties until a final product is reached. Initially a promising compound is identified and experimentally tested in different in vitro models, and after that preclinical studies are initiated most often by the use of different mouse models. Until this point, only small amounts of the compound need to be synthesized, and the purity requirements are lower than those required in clinical studies conducted in humans. There are many steps in drug development that are critical, e.g., identifying and isolating the active compound, investigating whether a particular isomer is more potent than the other, further have a permissible degree of purity, stability, and also that said compound can be manufactured in large scale. These are not trivial steps and many promising compounds/drugs fail to reach the market due to manufacturing problems as described above.

SUMMARY OF THE INVENTION

The present invention is based on the insight that the mixture of E and Z forms of Formula 1 can be transferred into the E-form of their di-hydrochloride salts of high steric purity.

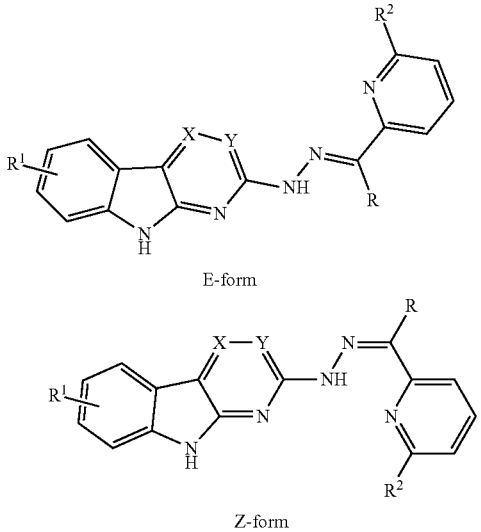

Formula 1

A first object of the present invention is to provide well-defined and stable pharmaceutical compositions comprising a high content of the pharmaceutically active isomer (E) of compounds or a pharmaceutically acceptable salt thereof represented by general formula 1, wherein:

R is H or methyl or methylene substituted by $C_1$-$C_4$ straight or branched alkyl, $R^1$ is selected from the group consisting of H, $C_1$-$C_4$ straight or branched alkyl, methoxy, methoxy substituted with from one to three fluorine, bromine, halogen;

$R^2$ is H or $C_1$-$C_4$ straight or branched alkyl;

X is CH or N;

Y is CH or N, and wherein at least 95% by weight (w/w) of the pharmacologically active compound or pharmaceutically acceptable salt thereof is in the form of the E-isomer, as defined in present claim 1.

The pharmaceutical compositions are intended to be used in the treatment of cancer. In one aspect at least 96%, or 97%, or 98%, or at least 98.5% by weight of said compound is in the E-form. In yet another aspect at least 99%, preferably at least 99.5%, most preferably at least 99.8% by weight of the pharmacologically active compound is in the form of the E-isomer. Ideally 100% by weight of said compound is in the form of the E-isomer. The pharmaceutical composition of the present invention may also further comprise at least one pharmacologically acceptable excipient and/or carrier.

According to a preferred embodiment of the invention the compound of the general Formula 1 may be additionally substituted by $C_1$-$C_4$ straight or branched alkyl at one of positions 6, 7, 8, 9 of the mono-, di- or tri-azacarbazolyl not substituted by $R^1$.

Preferred compounds of general Formula 1, as well as 1a and 1b, are listed in Table 1.

In one embodiment R and $R^1$ are $CH_3$, and $R^2$ is H. Preferably R is $CH_3$ and $R^1$ is 6-$CH_3$, and $R^2$ is H. More preferably X and Y are N.

In another embodiment R is $CH_2CH_3$, $R^1$ is $CH_3$ and $R^2$ is H. Preferably R is $CH_2CH_3$, $R^1$ is 6-$CH_3$ and $R^2$ is H. More preferably X and Y are N.

In yet another embodiment R is $CH_2C(CH_3)_3$, $R^1$ is $CH_3$ and $R^2$ is H. Preferably R is $CH_2C(CH_3)_3$, $R^1$ is 6-$CH_3$ and $R^2$ is H. More preferably X and Y are N.

Most preferred compounds of the present invention are compounds A, B and C (See Table 1).

In one embodiment, the pharmaceutical composition of the present invention comprises a pharmacologically active compound of general Formula 1 in the form of a pharmaceutically acceptable salt in crystalline form. The salt may be any salt suitable for stabilization of the free base of Formula 1, i.e., acidic salts, such as for example chlorides, nitrates and sulfates. The salt may be a mono- or di salt. Preferably, the salt is a mono or di-hydrochloride salt. Most preferably a di-hydrochloride salt.

The excipient(s) may be any of mannitol, glucose, sucrose or other suitable sugar derivatives. In a preferred embodiment the excipient is D-mannitol. The concentration of D-mannitol may be in the range of 0.5-20% (w/v). Preferably the concentration is in the range of 1.0-15% (w/v) by weight. More preferably the concentration is in the range of 3-10% (w/v). Most preferably the concentration is in the range of 4-6% (w/v). The concentration of D-mannitol is in another aspect more preferred to be about 5% (w/v).

TABLE 1

Exemplary compounds of the invention

| Compound | R | $R^1$ | $R^2$ | X | Y |
|---|---|---|---|---|---|
| A | $CH_3$ | 6-$CH_3$ | H | N | N |
| B | $CH_2CH_3$ | 6-$CH_3$ | H | N | N |
| C | $CH_2C(CH_3)_3$ | 6-$CH_3$ | H | N | N |
| D | $CH_3$ | 7-Cl | H | N | N |
| E | $CH_3$ | 6-Cl | H | N | N |
| F | $CH_3$ | 8-$OCH_3$ | H | N | N |
| G | $CH_3$ | 8-$OCF_3$ | H | N | N |
| H | $CH_3$ | 9-Br | H | N | N |
| I | $CH_3$ | 8-Cl | H | N | N |
| J | $CH_3$ | 8-$CH_3$ | H | N | N |
| K | H | 6-$CH_3$ | H | CH | CH |

The present invention further provides a process for preparing the pharmaceutical composition described above. The process comprises the following steps:

i. providing a solution of a compound of general formula 1 as a free base, ii. reacting the solution with hydrochloric acid in ethanol in sufficient amounts to form a compound of general formula 1b, i.e., a di-hydrochloride salt, and wherein the di-hydrochloride salt precipitates spontaneously;

iii. stripping the precipitate comprising the di-hydrochloride salt obtained in step (ii) of solvent, iv. dissolving the precipitate comprising the di-hydrochloride salt of step (iii) in an aqueous solvent, optionally comprising a pharmaceutically acceptable excipient, and v. freeze drying the mixture thereby obtaining a lyophilized powder or cake.

The solvent for the free base of general formula 1 may for example be methanol. The stripping of the precipitate i.e., step (iii) may for example be in vacuo made by means of an air or inert gas bleed.

The amount of the E-isomer is in the same ranges as for the pharmaceutical composition described above.

In one embodiment, the aqueous solvent is water. Preferably sterile water.

The excipient(s) can be as described above. The order of dissolving the precipitate is not limiting in the process and may be changed. The precipitate may for example be in solid form, mixed with the excipient in for example solid form, and added to an aqueous solvent under stirring. Or, the excipient may be dissolved in an aqueous solution to which the solid precipitate is added and dissolved under stirring.

A further object is to provide a pharmaceutical formulation for injection or infusion in form of an aqueous solution of said storage-stable pharmaceutical composition.

By reconstituting the lyophilized powder of step (v) in an aqueous solvent, for example water for injection (WFI), a pharmaceutical formulation is obtained.

The concentration of the pharmacologically active compound may be in the range of 0.05 to 40 mg/ml. In one embodiment the concentration of the pharmacologically active compound is in the range of 0.1 to 30 mg/ml. More preferably the pharmacologically active compound may be in the range of 0.5-20 mg/ml. Even more preferably the pharmacologically active compound may be in the range of 0.75-10 mg/ml. The concentration of said pharmacologically active compound may most preferably be about 1 mg/ml.

The pH of the formulation is below 4. The pH of said formulation depends on the concentration of the pharmacologically active compound and is usually in the range of 0.5-4. For example a formulation having a concentration of 1 mg/ml of the pharmacologically active compound has a pH in the range of 2-3.

The reconstitution may be performed in one or several steps such as dissolving the lyophilisate by adding a first amount solvent, thereafter adding solvent to a desired final concentration.

The aqueous solvent for reconstituting the lyophilized powder comprising said pharmaceutically active compound may also comprise a pharmaceutically acceptable excipient as described above.

Another object of the present invention is to provide a method for alleviating, reducing or treating cancer in a subject by using the pharmaceutical composition of the invention, alone or in combination with another anticancer treatment.

The administration route of the pharmaceutical formulation may be by infusion or injection. However, any suitable route for administration of the formulation or composition may be used. The formulation or composition may be administered for example intra-arterial, intramuscular, intrapleural, oral, rectal, enteral, intra-lesional or intra-tumoral, and intrathecal administration.

Another object of the present invention is to provide a precipitate exemplified by general Formula 1b, Formula 1b

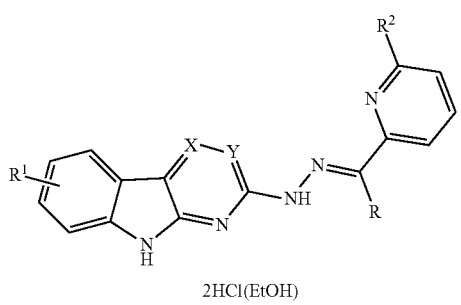

2HCl(EtOH)

wherein at least 95% by weight (w/w) of the pharmacologically active compound of general Formula 1b is in the form of the E-isomer.

The amount of the E-isomer may be in same the ranges as for the pharmaceutical composition described above.

The compound of general Formula 1b is a precipitate of the indole derivative of Formula 1, wherein the substitutions R, $R^1$, $R^2$, X and Y are as defined above for Formula 1. Preferred compounds of general Formula 1b are listed in Table 1. Most preferred compounds of general Formula 1b are substituted as compounds A, B and C in Table 1.

Another object of the present invention is to provide a process for preparing the precipitate comprising said compounds or pharmaceutically acceptable salts described above, said process corresponds to process steps i) to iii) described above for the pharmaceutical composition.

In one aspect, the di-hydrochloric acid in ethanol (i.e., step ii) is added in two steps, wherein 1.0-1.15 equivalents of hydrochloric acid in ethanol is added in the first step and 2.0 to 2.5 equivalents of hydrochloric acid in ethanol is added in the second step. Alternatively, addition may be performed in one step or several steps. The salt precipitates spontaneously in step (ii).

The precipitate described above can also be used in a pharmaceutical composition.

The precipitate can be used directly or after drying before further processing to a lyophilisate.

The ethanol content of said precipitate is in the range of 2-15% by weight of said precipitate. Preferably in the range of 4-13% or, 9-11% by weight of said precipitate. In one embodiment the amount ethanol is 10.4-10.6% by weight of said precipitate.

The present invention further provides a lyophilisate comprising a compound of general Formula 1a, Formula 1a

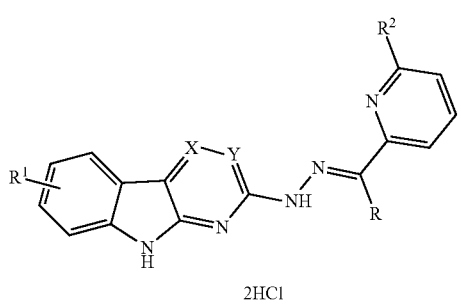

2HCl wherein at least 95% by weight (w/w) of the pharmacologically active compound of general Formula 1a is in the form of the E-isomer. The amount of the E-isomer may be in the same range as for the pharmaceutical composition described above.

The compound of general Formula 1a is a di-hydrochloride salt of the indole derivatives described above for Formula I.

Most preferred compounds are substitutes as described for formula 1 and 1b above.

The present invention further provides a process for preparing said lyophilisate, the process comprise the following steps:
a) dissolving a precipitate of general Formula 1b in an aqueous solvent,
b) filtering the resulting solution,
c) freeze drying the solution of step b) to obtain a lyophilisate comprising a compound of general Formula 1a.

In one aspect the precipitate may be dissolved in the aqueous solvent under stirring in step a). The process is further described in the detailed description.

The precipitate of step a) may be substituted as any of the compounds described for Formula 1 or 1b. In another aspect the precipitate may comprise one or a combination of the described compounds. In yet another aspect separate precipitates comprising different compounds of the present invention may be mixed.

The aqueous solvent may further comprise at least one pharmacologically acceptable excipient. The excipient and concentration of excipient may be as described above.

The resulting solution of step b) may preferably be filtered through at least one sterile filter, in some embodiments the resulting solution of step b) is filtered through two sterile filters. The resulting solution may for example be recovered in a sterile bulk before step c). The solution of step b) may also be filled into vials suitable for freeze drying.

Yet another object of the present invention is to provide a precipitate or lyophilisate as described above for use in a pharmaceutical composition.

The pharmaceutical composition (i.e., the lyophilisate) and precipitate of the present invention are stable for at least 12 months in room temperature. Preferably the pharmaceutical composition (i.e., the lyophilisate) and precipitate are stable for at least 24 months in room temperature.

Yet another object of the present invention is to provide a pharmaceutical composition, i.e., a lyophilisate comprising said compounds for use in treating cancer.

In one aspect, the lyophilisate of the present invention may comprise only one pharmacologically active compound of the present invention such as for example compound A2, B2 or C2. In another aspect the lyophilisate of the present invention may comprise a combination of compounds of the present invention. In yet another aspect, the lyophilisate comprising said compounds or pharmaceutically acceptable salts of the present invention may comprise at least one of the compounds of the present invention in combination with at least one other pharmacologically active compound for use in cancer treatment.

The compounds of the present invention may be administered separately or as a mixture. The compounds may further be administered at the same time or prior to or after another medicament or anticancer treatment.

The pharmaceutical composition, precipitate or the formulation described above may for example be used for prevention or in the treatment of a disease or disorder characterized by pathologically proliferating cells.

The pharmaceutical formulation may be suitable for infusion or injection by reconstituting said composition in an aqueous solvent. Preferably the formulation is used for infusion.

The final concentration of the pharmacologically active compound may be in the range of 0.5-30 mg/ml.

The pharmaceutical composition and formulation may have a pH in the range of 0.5-4. Preferably the pH is in the range of 1-3. As mentioned above, the pH depends on the concentration of the pharmaceutically active compound, and for example the pH for a 1 mg/ml formulation is in the range of 2-3.

The pharmaceutical composition or formulation may further comprise a co-therapeutic agent.

Preferably, the pharmaceutical composition and formulation of the present invention is used for treating cancer.

The cancer may be a solid, liquid and haematological tumor.

Further, the medicament, pharmaceutical formulation, composition, precipitate or lyophilisate described above may be used in combination with another anticancer treatment such as chemotherapy, immunological or immunomodulating therapy, hormone therapy, surgical removal of the tumour, photodynamic therapy, laser therapy, hyperthermia, cryotherapy, angiogenesis inhibition, radiation therapy, or a combination of these.

The present invention further provides a method for treating a disease or disorder characterized by pathologically proliferating cells, such as cancer, in which an effective amount of a pharmacologically active compound of the present invention is administered to a subject in need of such treatment.

The effective amount of said pharmacologically active compound or compounds varies among individuals and cancer form. For example the amount is about 0.1-10 mg/kg body weight, preferably 0.5-5 mg/kg and more preferably 1-4 mg/kg body weight. The total dose given to a subject may be in the range of 5-800 mg, depending on the subject's condition and cancer form and independent of the weight of said subject. In one aspect the dose administered to a subject is in the range of 30 to 300 mg. The dose can be even lower when given in combination with another cancer treatment as exemplified below.

In another aspect, the invention provides a method for the treatment of cancer described above in combination with another anticancer treatment.

The different embodiments described above can be combined with each other or used separately.

The details of one or more embodiments of the invention are set forth in the detailed description below. Other features, objects, and advantages of the invention will be apparent from the description and drawings, and from the appended claims, hereby incorporated by reference.

BRIEF DESCRIPTION OF FIGURES

The following figures are illustrative of aspects of the invention and are not meant to limit the scope of the invention as encompassed by the claims.

DETAILED DESCRIPTION

It is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

All references cited are incorporated herein by reference in their entirely and for all purposes to the same extent as if each individual publication or patent or patent application was specifically and individually indicated to be incorporated by reference in its entirety for all purposes.

The present invention is best understood by reference to the following definitions, the Figures and exemplary disclosure provided herein.

In this specification, the compound of general Formula 1 is intended to include any pharmaceutically suitable precipitate, solvate, salt or prodrug thereof.

Figure 1:
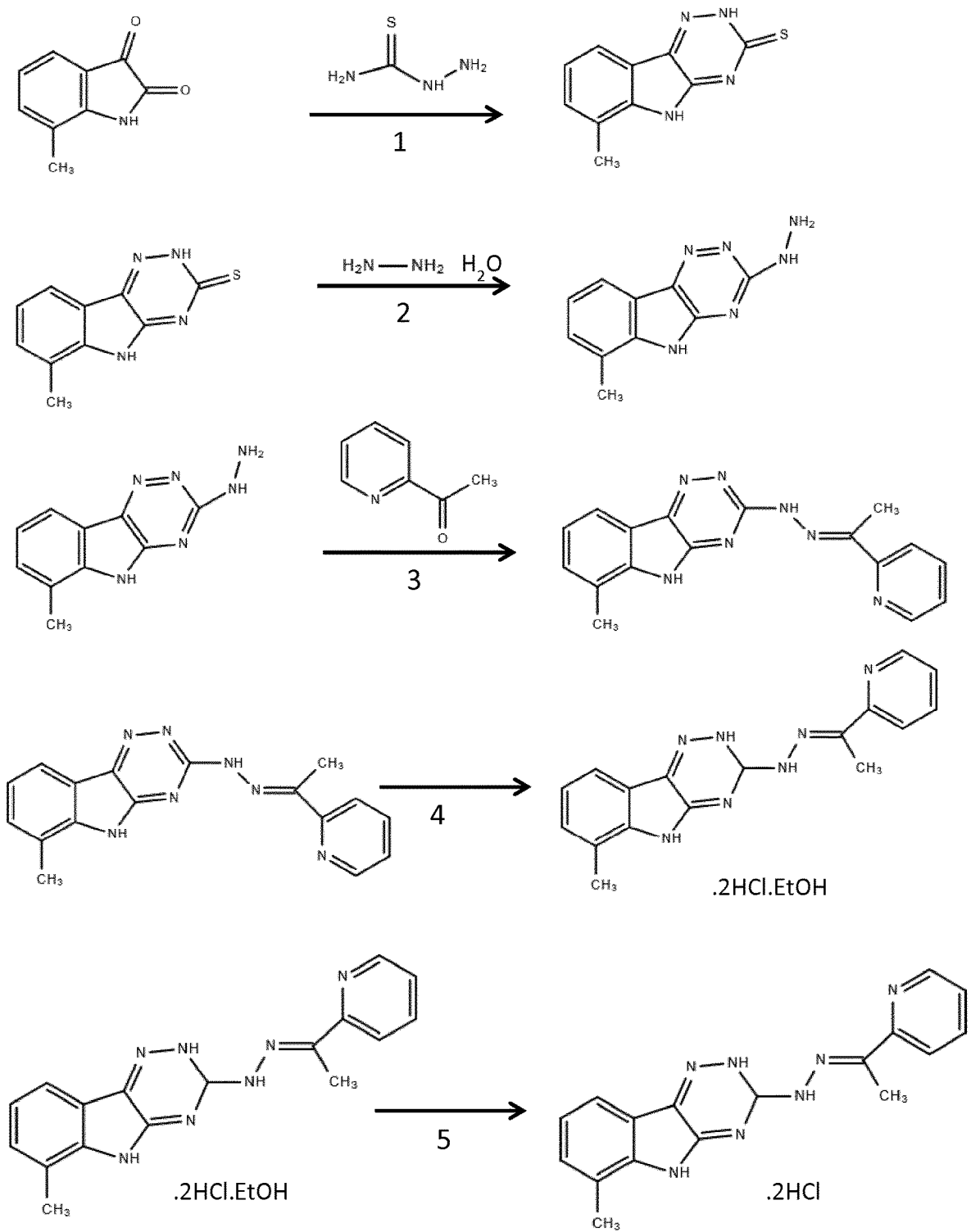
FIG. 1 shows the synthetic route for synthesis of the precipitate (A1) of compound A, and the salt formation step of the precipitate to the corresponding salt, i.e., lyophilisate (A2).

In this specification the term precipitate means the di-hydrochloride ethanol co-crystal compounds, or the di-hydrochloride ethanolate or the di-hydrochloride ethanol solvate obtained by precipitation e.g., the product of the precipitation step in reaction 4 in FIG. 1. The compounds may be a precipitate of any compound of formula 1 of the present invention.

In this specification the term pharmaceutically acceptable compounds comprise precipitates, solvates and lyophilisates of the compounds described in the present specification.

In this specification the term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers). The term "stereoisomer" refers to isomers of identical constitution that differ in the arrangement of their atoms in space.

In this specification, unless otherwise stated, the term "pharmaceutically acceptable excipient" means a non-toxic, inert solid, semi-solid or liquid filler, diluent, encapsulating material or formulation auxiliary of any type.

In this specification, unless otherwise stated, the term "pharmaceutically active compound" encompasses any substance that will produce a therapeutically beneficial pharmacological response when administered to a host, including both humans and animals.

In this specification the term "administering" or "administration" means providing a drug to a subject in a manner that is pharmacologically useful.

In this specification, unless otherwise stated, the term "cytotoxic compound" refers to a compound that has the ability of arresting the growth of, or killing, cells, i.e., having high cytotoxic activity.

In this specification, unless otherwise stated, the term "derivative" refers to a compound formed from the original structure either directly, by a chemical reaction of the original structure, or by a "modification" which is a partial substitution of the original structure, or by design and de novo synthesis. Derivatives may be synthetic, or may be metabolic products of a cell or an in vitro enzymatic reaction.

In this specification the term "cancer" is meant to mean any malignant neoplastic disease, i.e. any malignant growth or tumor caused by abnormal and uncontrolled cell division. The term "cancer" is in particular meant to include both solid, localized tumors, and non-solid cancer forms. For example said cancer forms may be selected from the group consisting of leukemia (ALL, AML, CLL, CML, CMML), T-cell leukemia, multiple myeloma, ovarian carcinoma, prostate cancer, cervix adenocarcinoma, squamous cell carcinoma, breast cancer, colorectal cancer, small bowel cancer, anal cancer, gastric cancer, kidney cancer, malignant melanoma cancer of the renal pelvis and ureter, urethral cancer, bladder cancer, liver cancer, appendix cancer, pancreas cancer, lung cancer, cancer of the oesophagus, lip/oral cavity cancer, nasal cancer, larynx cancer, brain/central nervous system cancer, skin cancer, thyroid and thymus cancer, sarcoma, head and neck cancer, Non-Hodgkin lymphoma (NHL), Hodgkin lymphoma, and pseudomyxoma peritonei.

The present invention provides a process for preparing a pharmaceutical composition which is favorable to the E-isomer. Single crystal X-ray confirmed that the E-isomer was predominant in the solid state.

Figure 2A:
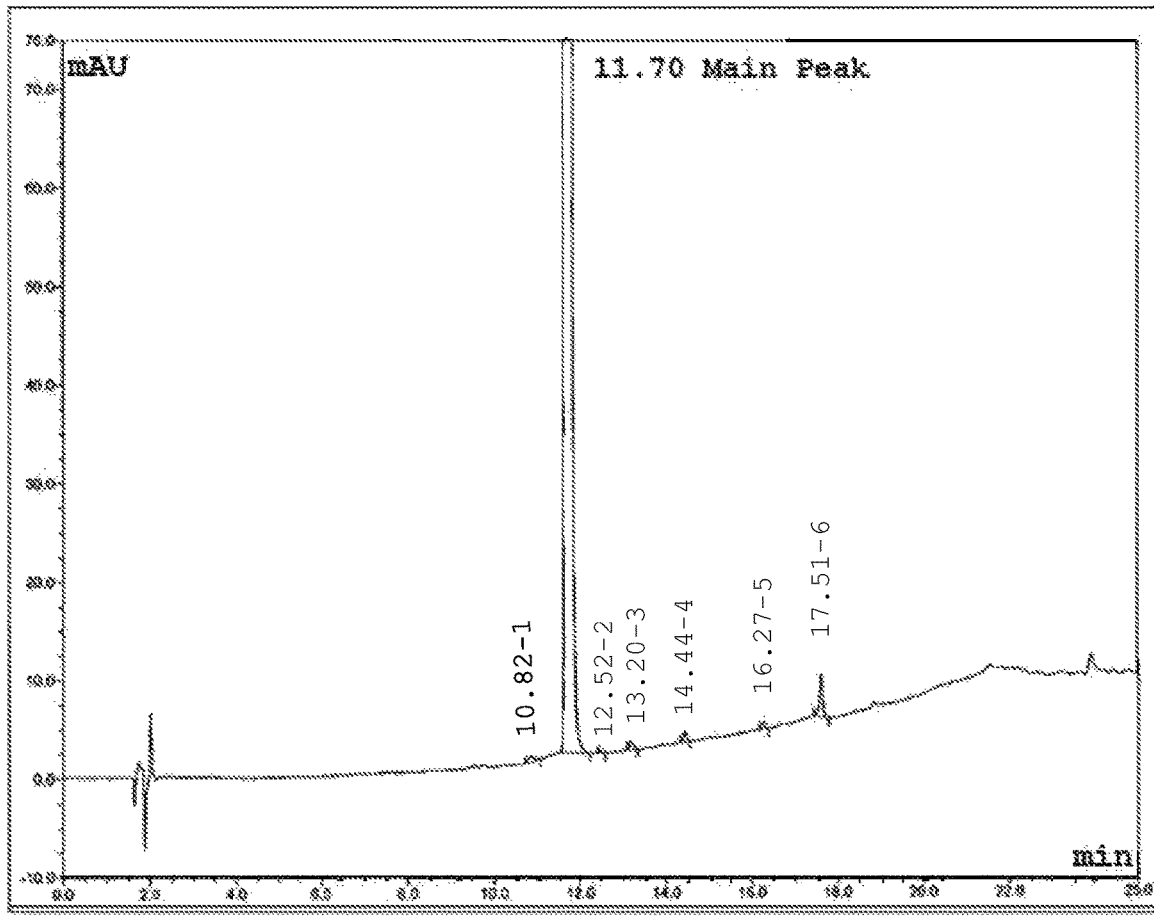
FIG. 2a depicts a HPLC-chromatogram showing 99.8% purity of compound A1.

By using the process of the present invention a well-defined and stable pharmaceutical composition comprising at least 95% by weight (confirmed by HPLC, See FIG. 2) of the pharmaceutically active compound (E-isomer), is obtained.

EXAMPLES

Example 1 Synthesis of Compound A

In the first experiments compound A (free base) was diluted in acetone/acetylate/acetone nitrile, the E-isomer but not the Z-isomer was soluble in this solvent combination, and was easily filtered of. The final E-isomer content by using this solvent combination was about 92%. The described solvent combination worked well during small scale production but not for scaling up production due to high amounts of solvent needed. Therefore, synthesis of compound A based on the synthesis of 1, 2, 4-triazino[5,6-b]indole derivatives described by Kgokong, et al., 2005 was developed by the inventors (See FIG. 1). The inventors developed a procedure using methanol (MeOH) as solvent, and hydrochloric acid in ethanol (HCl/EtOH) as carrier of HCl (EtOH also serves as an anti-solvent). In the subsequent development of the scaling up process the reaction volume efficiency was improved. Moreover, a suitable method for conversion of the free base (A) to the final hydrochloride precipitate (A1) on a large scale was also developed (See FIG. 1, Examples 1 and 2). The free base (A) was not soluble in MeOH alone, but upon addition of about 1 equivalent of HCl/EtOH a clear solution was obtained.

Due to observed disulphide species, the reaction may be performed under nitrogen to avoid air oxidation. The wet cake produced by reaction step 1 may also be dried in vacuo, or the wet cake may be further processed without prior drying. By drying in vacuo the generation of impurities is minimalized, since impurities may be generated during air-vented drying. Reacting the product compound of reaction step 2 with a slight excess of 2-acetylpyridine (1.5 eq.) in ethanol (20 mL/gram compound) at 50° C. gave product formation, but too slow conversion (~8%) after 5 hrs.

FIG. 1 shows reaction steps 1-3 of the synthesis of compound A (mixture of E and Z isomers; IUPAC systematic name: 2-[(1E,Z)-1-(2-{6-methyl-5H-[1,2,4]triazino[5,6-b]indole-3-yl}hydrazine-1-ylidene)ethyl]-pyridine).

Step 1. To an aqueous suspension of 7-methylisatin (4.75 kg, 29.5 mol) was added 2.85 kg (31.3 mol) of thiosemicarbazide and 6.15 kg (44.5 mol) of potassium carbonate. The stirred mixture was heated under reflux for 3 hrs, then cooled to room temperature. Acetic acid (100%, 3.3 kg, 55.0 mol) was slowly added until a pH of 7.1 had been reached. The suspension was filtered on a pressure filter and the filter cake washed with water (19.4 kg) to obtain 7.6 kg of wet 6-methyl-2H,3H,5H-[1,2,4]triazino[5,6-b]indole-3-thione.

Step 2. The wet filter cake from the preceding step corresponding to about 4.6 kg of dry 6-methyl-2H,3H,5H-[1,2,4]triazino[5,6-b]indole-3-thione was suspended in 57.1 kg of hydrazine monohydrate and the mixture stirred at 89° C. for 18 hrs. The reaction mixture was cooled to room temperature and the product isolated by centrifugation, washed with water (15.9 kg) and ethanol (18.4 kg), and drained at 1450 RPM). The wet filter cake (7.8 kg corresponding to 3.8 kg dry weight) of 3-hydrazinyl-6-methyl-5H-[1,2,4]triazino[5,6-b]indole was transferred back to the cleaned reactor and dried under vacuum.

Step 3. To the dried 3-hydrazinyl-6-methyl-5H-[1,2,4]triazino[5,6-b]indole from Step 2 was added water (76.85 kg), acetic acid (100%, 6.70 kg, 111.6 mol) and 2-acetylpyridine (10.75 kg, 88.7 mol). The mixture was stirred for 3 hrs at 48.5° C., cooled to room temperature and NaOH (27%, 6.3 kg, 110 mol) slowly added to reach pH 7.0 while maintaining the temperature between 20 and 25° C. The mixture was stirred for further 1¼ hrs at this temperature and the product isolated by centrifugation. After washing with a mixture of water (7.3 kg) and ethanol (5.8 kg) the cake was drained at 1450 RPM, then dried in a vacuum oven at 47° C. for 66 hrs to yield 5.82 kg of the title compound in form of a beige/greenish solid material.

Step 4 in FIG. 1 shows the synthesis of Compound A1, the ethanol co-crystal of compound A (IUPAC systematic name: 2-[(1E)-1-(2-{6-methyl-5H-[1,2,4]triazino[5,6-b]indole-3-yl}hydrazine-1-ylidene)ethyl]-pyridine di-hydrochloride)

To 2-[(1E,Z)-1-(2-{6-methyl-5H-[1,2,4]triazino[5,6-b]indole-3-yl}hydrazine-1-ylidene)ethyl]-pyridine) (5.80 kg) was added ethanolic HCl (12.4 kg, 1.05 equiv.) and the mixture stirred at 28-30° C. for half an hour until a clear solution was obtained. The solution was filtered and additional ethanolic HCl (28.95 kg, 2.45 equiv.) was added at 25° C. over 1 h and 40 min under stirring. During the first addition of 1.05 equiv. HCl/EtOH the majority of the Z-isomer present transforms to the E-isomer and some monohydrochloride salt is formed. The di-hydrochloride salt precipitates spontaneously by the addition of 2.45 equiv. HCl in EtOH. Molarity determination of HCl in EtOH by titration with 0.1 M NaOH phenolohthalein indicator was calculated to be about 1.1 to 1.4 M HCl. Stirring was continued at the same temperature for 15 min and ethanol (45.8 kg) added. The so formed suspension was cooled to about 0 to −5° C. and stirred for 1 h. The product isolated by centrifugation was washed with ethanol (0 to 5° C., 45 kg), then drained at 1450 RPM. The cake was dried in vacuum at 37° C. for 42 hrs to yield 7.57 kg of the title compound (about 108% on residual solvent-free basis or 98% based on mono-EtOH, di-hydrochloride as a yellow to orange solid.

The ethanol co-crystalline di-hydrochloride precipitate obtained has a content of ethanol from about 2% to 20% by weight.

Reaction step 5 in FIG. 1 illustrates the formation of the freeze dried composition comprising a compound of general formula 1a.

Analysis of Isomer Content by HPLC

During the process development, analysis of compound A and compound A1 caused analytical problems due to e.g. sample instability, poor solubility, isomerisation, HPLC, etc. Therefore a more robust HPLC method was developed by the inventors based on an XBridge C18, 3.5 µm, 150×4.6 mm column. The problem was further solved by using 2% formic acid in MeOH as diluent, and switching from uncoated standard HPLC sample vials to coated (silanized) vials from Agilent.

Agilent 1200/1260 chromatographic system or equivalent was used.

When using the acidic HPLC to analyse compound A it was found that ~7% was in the form of the Z-isomer (sample preparation in 0.1% TFA/H$_2$O). After 2 days the same sample was re-analysed showing ~2% of the Z-isomer, and the beginning of hydrolysis to compound A1 (~1% detected). This showed that acidic conditions (pH in the range of 1-4) transforms the unwanted Z-isomer to the desired E-isomer. When the subsequent salt formation (reaction step 4) was performed (using HCl in ethanol), the isomeric content was lowered to <0.5%. This means that a relatively large content of the unwanted isomer (such as 5%) can be allowed of compound A, B or C since it is being converted to the desired isomer upon addition of HCl in ethanol. The addition of HCl in ethanol forms a di-hydrochloride precipitate (such as compounds A1, B1 and C1).

HPLC Purity

HPLC purity was calculated as 100%—total impurities. All peaks below 0.05% and peaks present in the matrix are excluded from the calculations. The content of each impurity was calculated as percentage of the total peak area (area %). Total impurities are the sum of impurities ≥0.05%.

Impurities

The final result of each impurity is the average of four results. Total impurities are reported as the sum of impurities ≥0.05%.

Residual Solvents

Analysis of compound A1 showed that it is a di-hydrochloride ethanol co-crystal composition (precipitate). The theoretical ethanol content of compound A1 is 10.6%, which is consistent with the formation of an ethanol co-crystal (precipitate) as described above.

During the process development of compositions comprising compound A it was surprisingly shown that the di-hydrochloride ethanol co-crystal (e.g., A1) is less hygroscopic and significantly more stable towards hydrolysis and degradation of isomeric purity.

It was concluded that high levels of ethanol could be tolerated in the drug substance (precipitate) since it is removed during the subsequent freeze drying, which is part of the manufacturing process of the final drug product (lyophilisate).

The methanol levels showed to be relatively high; typically methanol contents of composition A1 was 1.4-1.8%. Prolonged drying cycles did not significantly decrease the methanol content. However, as in the case with ethanol, the subsequent freeze drying cycle used during manufacturing of the final drug product (e.g., A2), efficiently removes the methanol down to levels below the ICH Q3B guideline.

Conclusion

Based on the fact that both the ethanol and methanol levels are well below the ICH Q3C guideline in the final drug product and given that this is carefully monitored, it was concluded that the higher levels could be allowed in the drug substance (i.e., precipitate of compound A1). All other limits stated in the specification are within Ph. Eur or USP standards.

Identification

The identity of a sample was based on a visual inspection of the main peak of a sample preparation and the main peak of the sample preparation for identification. Compound A1 is represented by a single peak in the chromatogram (See FIG. 2a).

Example 2

Stability

The stability study of the di-hydrochloride ethanol co-crystal precipitate and of the lyophilized di-hydrochloride salt was conducted in accordance with the International Conference on Harmonizations (ICH) guideline Q1A (R2) Stability Testing of New Drug Substances and Products. All analytical instruments used to analyze the stability samples during the study are qualified in compliance with current cGMP.

The stability study consists of two parts, one long-term—(5° C., 24, 36 months) and one accelerated study (25° C./60% RH, 6 months).

The di-hydrochloride ethanol co-crystal precipitate of compound A (A1) was packed in heat sealed double polyethylene bags inside a heat sealed foiled laminate pouch placed in a closed HDPE container. The samples were stored at the long term condition 5° C. and at the accelerated condition 25° C./60% RH. The appearance was yellow to orange solid during the whole test period. Analysis performed due to the X-Ray powder diffraction result for 25° C./60% RH sample which had an unexpected low level of crystallinity. The level of crystallinity has no direct effect on the quality or stability of the drug substance but is controlled as part of the development work. The 36 month stability data obtained are summarized in table 2a below.

Table 2b shows the stability data for the di-hydrochloride ethanol co-crystal precipitate at 25° C. and 60% RH over a period of 6 months. The appearance was yellow to orange solid during the whole period.

Conclusion

The present composition comprising compound A1 is stable for at least 24 months (Table 2a). During this period no significant breakdown of compound A1 occurred at either 2-8° C. or 25° C./60% RH (6 months). It is suggested that the composition of compound A1 should be stored and transported at 2-8° C. However, 24 hours of storage at temperatures up to 25° C. should be of no concern.

Example 3

Manufacture of a Pharmaceutical Composition of the Ethanol Co-crystal Precipitate of 2-[(1)-1-(2-{6-methyl-5H-[1,2,4]triazino[5,6-b]Indole-3-yl}hydrazine-1-ylidene)ethyl]-pyridine di-hydrochloride A multiple of 225.6 mg of ethanol co-crystal precipitate of mainly 2-[(1E)-1-(2-{6-methyl-5H-[1,2,4]triazino[5,6-b]indole-3-yl}hydrazine-1-ylidene)ethyl]-pyridine di-hydrochloride (A1) (corresponds to 160 mg free base, A) was dissolved in a solution of mannitol (500 mg) in water for injection (Ph. Eur., 10 ml), the solution was sterilized by filtration through two 0.2 μm filters and filled into a corresponding number of sterilized vials, then freeze dried (obtaining a salt of compound A2).

TABLE 2a

| | | \multicolumn{9}{c}{Time (months)} | | | | | | | | |
|---|---|---|---|---|---|---|---|---|---|---|
| | | 0 | 1 | 3 | 6 | 9 | 12 | 18 | 24 | 36 |
| RRT 0.92-0.93 | ≤1.0 | 0.05 | <0.05 | <0.05 | <0.05 | <0.05 | <0.05 | 0.07 | <0.05 | 0-07 |
| RRT 1.13 | ≤1.0 | <0.05 | <0.05 | <0.06 | <0.06 | <0.05 | 0.05 | 0.05 | 0.05 | <0.05 |
| RRT 1.23-1.24 | ≤1.0 | 0.05 | 0.05 | 0.06 | 0.06 | 0.05 | 0.06 | 0.06 | 0.06 | 0.06 |
| RRT 1.39 | ≤1.0 | <0.05 | <0.05 | <0.05 | <0.05 | <0.05 | <0.05 | 0.05 | <0.05 | <0.05 |
| RRT 1.47-1.51 | ≤1.0 | 0.17 | 0.10 | 0.10 | 0.36[2] | 0.09 | <0.05 | 0.06 | 0.05 | 0.06 |
| Total impurities | ≤2.0 | 0.26 | 0.15 | 0.16 | 0.42 | 0.14 | 0.10 | 0.29 | 0.16 | 0.18 |
| Water content (% w/w) | | 2.53 | 2.34 | 2.18 | 2.50 | 2.88 | 2.65 | 2.73 | 3.37 | 2.46 |

[2]The relative area for the impurity at RRT = 1.47-1.51 is higher than expected. The sample preparation and HPLC analysis was repeated by another analyst, which confirmed the result. Fluctuating peak area for this impurity was observed during the test method validation.

The inventors developed a new freeze drying process since the ordinary methods used by prior art required more than 300 hrs of drying. The new method is more aggressive and outlined in table 3 below.

TABLE 2b

| | | \multicolumn{4}{c}{Time (months)} | | | |
|---|---|---|---|---|---|
| | | 0 | 1 | 3 | 6 |
| RRT 0.92-0.93 | ≤1.0 | 0.05 | <0.05 | 0.05 | 0.07 |
| RRT 1.12 | ≤1.0 | <0.05 | <0.05 | <0.05 | 0.05 |
| RRT 1.24 | ≤1.0 | 0.05 | 0.05 | 0.06 | 0.05 |
| RRT 1.38 | ≤1.0 | <0.05 | <0.05 | 0.05 | <0.05 |
| RRT 1.49-1.51 | ≤1.0 | 0.17 | 0.10 | 0.06 | 0.36[2] |
| Total impurities | ≤2.0 | 0.26 | 0.16 | 0.22 | 0.52 |
| Water content (% w/w) | | 2.53 | 2.41 | 2.30 | 2.45 |

[2]The relative area for the impurity at RRT = 1.47-1.51 is higher than expected.

The sample preparation and HPLC analysis was repeated by another analyst, which confirmed the result. Fluctuating peak area for this impurity was observed during the test method validation.

By having max negative pressure and relatively high temperature, annealing the temperature as in Table 3, the freeze drying step was decreased to 19 hrs.

Contact with metallic surfaces was avoided. Ethanol and minor amounts of methanol present were removed by the freeze drying process.

The vials were crimp sealed under nitrogen and stored at 5° C.; no degradation was seen after storage for 24 months.

Glucose and mannitol were evaluated as excipients, both alone and in combination with NaCl. The best result regarding solubility, texture of the lyophilised cake and suppression of impurity formation was obtained with 5% (w/v) mannitol as additive. A higher degree of collapse of the freeze-dried cake was observed with glucose as bulking agent. Addition of NaCl caused solubility problems since the increase in pH generated by NaCl decreased the solubility of compound A2.

The lyophilised powder for reconstitution and injection (corresponding to 160 mg free base of compound A) were stored at conditions 2-8° C. up to 24 months. The appearance was yellow to orange freeze dried cake during the whole test period and after reconstitution yellow to orange solution without visible particles.

TABLE 3

| Step type | Temperature (T ° C.) | Time (h) | Vacuum (mbar) |
|---|---|---|---|
| Shelves | 5 | / | / |
| Freezing step | 5 | 0.30 | / |
| Freezing ramp | −45 | 0.50 | / |
| Freezing step | −45 | 4 | / |
| Freezing ramp (Annealing) | −25 | 1 | / |
| Freezing step (Annealing) | −25 | 2 | / |
| Freezing ramp (Annealing) | −45 | 1 | / |
| Freezing step | −45 | 4 | / |
| Chamber Vacuum | −45 | / | 0.200 |
| Primary drying | −45 | 0.10 | 0.200 |
| Primary drying ramp | 25 | 3 | 0.200 |
| Primary drying step | 25 | XX* | 0.200 |
| Secondary drying ramp | 25 | 10 | max |
| End of cycle | | | |

Analysis performed due to the X-Ray powder diffraction result for 25° C./60% RH had an unexpected low level of crystallinity. The level of crystallinity has no direct effect on the quality or stability of the drug substance but is controlled as part of the development work. The reconstitution time was up to 3 minutes. No bacterial growth was detected and the sterility of the product was not influenced during the 24 months period in room temperature. The stability data obtained is summarized in Table 4a below.

TABLE 4a

| | \multicolumn{7}{c}{Time (months)} | | | | | | |
|---|---|---|---|---|---|---|---|
| | 0 | 1 | 3 | 6 | 12 | 18 | 24 |
| pH | 1.6 | 1.6 | 1.6 | 1.5 | 1.6 | 1.6 | 1.7 |
| Water content (%) | 0.33 | 0.41 | 0.47 | 0.37 | 0.53 | 0.43 | 0.39 |
| Assay (% w/w)[1] | 97.8 | 98.4 | 95.9 | 97.3 | 93.9 | 94.6 | 94.2 |

TABLE 4a-continued

| | Time (months) | | | | | | |
|---|---|---|---|---|---|---|---|
| | 0 | 1 | 3 | 6 | 12 | 18 | 24 |
| Total impurities (%) | 0.7 | 0.5 | 0.3 | 0.4 | 0.2 | 0.3 | 0.34 |
| Any individual purity (%) | 0.4 | 0.3 | 0.1 | 0.1 | 0.1 | 0.1 | 0.10 |
| Specified impurity* (%) | <0.5 | <0.05 | <0.05 | 0.08 | 0.08 | 0.10 | 0.09 |
| Z-isomer (%) RRT 0.92-0.93 | 0.1 | 0.1 | 0.1 | 0.1 | <0.05 | <0.05 | 0.05 |
| RRT 1.13 | 0.05 | <0.05 | <0.05 | <0.05 | <0.05 | 0.05 | <LOQ |
| RRT 1.23-1.24 | 0.06 | 0.05 | 0.08 | 0.05 | 0.06 | 0.05 | 0.05 |
| RRT 1.39 | | | | | | | |
| RRT 1.47-1.51 | 0.37 | 0.32 | 0.05 | <0.05 | <0.05 | 0.05 | 0.10 |

*Hydrolysis impurity 3-Hydrazinyl-6-methyl-5H-[1,2,4]triazino[5,6-b]indole

The LOQ is 0.05%, peaks <than LOQ was recorded as <0.05%

The lyophilised powder for reconstitution and injection (corresponding to 160 mg free base of compound A) were stored at accelerated conditions 25° C./60% RH (See Table 4b). The appearance was yellow to orange freeze dried cake during the whole test period and after reconstitution yellow to orange solution without visible particles. Analysis performed due to the X-Ray powder diffraction result for 25° C./60% RH had an unexpected low level of crystallinity. The level of crystallinity has no direct effect on the quality or stability of the drug substance but is controlled as part of the development work. The reconstitution time was up to 3 minutes. No bacterial growth was detected and the sterility of the product was not influenced during the 24 months period in room temperature. Surprisingly, the lyophilisate showed to be stable at least 24 months in room temperature. The stability data obtained is summarized in Table 4b below.

TABLE 4b

| | Time (months) | | | | | | |
|---|---|---|---|---|---|---|---|
| | 0 | 1 | 3 | 6 | 12 | 18 | 24 |
| pH | 1.6 | 1.6 | 1.6 | 1.5 | 1.6 | 1.5 | 1.6 |
| Water content (%) | 0.33 | 0.39 | 0.55 | 0.45 | 0.59 | 0.49 | 0.45 |
| Assay (% w/w)[1] | 97.8 | 97.2 | 95.4 | 98.3 | 94.6 | 93.9 | 94.5 |
| Total impurities (%) | 0.7 | 0.3 | 0.7 | 0.4 | 0.2 | 0.20 | 0.36 |
| Any individual purity (%) | 0.4 | 0.1 | 0.2 | 0.1 | 0.1 | 0.1 | 0.10 |
| Specified impurity* (%) | <0.5 | 0.1 | <0.05 | 0.08 | 0.08 | 0.10 | 0.10 |
| Z-isomer (%) RRT 0.92-0.93 | 0.1 | <0.05 | 0.1 | 0.1 | 0.10 | <0.05 | 0.05 |
| RRT 1.13 | 0.05 | <0.05 | <0.05 | <0.05 | <0.05 | nd | <LOQ |
| RRT 1.23-1.24 | 0.06 | 0.05 | 0.08 | 0.06 | 0.06 | 0.06 | 0.06 |
| RRT 1.39 | | | | | | | |
| RRT 1.47-1.51 | 0.37 | 0.13 | 0.05 | <0.05 | <0.05 | nd | 0.09 |

*Hydrolysis impurity 3-Hydrazinyl-6-methyl-5H-[1,2,4]triazino[5,6-b]indole

The LOQ is 0.05%, peaks <than LOQ was recorded as <0.05%. The pH should be in the range of 0.5-4, in the example above the concentration is about 16 mg/ml and the pH is in the range of 1.3 to 2.3 and water content below 1%. The Z-isomer is preferably less than 2%, however the inventors surprisingly found that acidic conditions favour the E-isomer.

The lyophilisate comprising compound A2 surprisingly showed to be less soluble in water after lyophilisation than prior to. Due to this, a structural investigation was conducted and this study showed that compound A2 changes its crystalline form during freeze-drying. The new crystalline form was less soluble in water, which explains the difference in solubility between the di-hydrochloride ethanol co-crystal precipitate (A1) and the di-hydrochloride salt (A2). Experiments indicated that this exhaustion of precipitates induced the change of morphous form. Results from the experiments also showed that the excipient (D-Mannitol) does not have any impact on the formation of the new morphic form. The best result concerning formation of impurities and texture of the freeze dried cake was obtained with the freeze drying cycle described in Table 3 and the mannitol content set at 5%.

Example 4

Preparation of a Pharmaceutical Formulation

It was found that compound A2 could be formulated in aqueous media to supress formation of by-products up to 24 hrs at 1 mg/ml. Also, it is understood that the pH is of significance for the stability of compound A2 in aqueous media with the best stability at pH around 1-4, higher concentration of the substance results in lower pH. 1 mg/ml of said aqueous solution has a pH about 2-3.

The resulting compound A2 is formulated as a sterile lyophilised powder, and a solution for injection or infusion was prepared by dissolving the lyophilized powder described above in an aqueous solvent such as water for injection. Each vial contains an amount pharmacologically active compound corresponding to 160 mg free base (A) prepared from a solution of 225.6 mg drug substance (A1), and 5% mannitol (w/v). The lyophilisate may be reconstituted in 10 ml aqueous solvent, and thereafter diluted to 1 mg/ml in an aqueous solvent optionally comprising a pharmacologically acceptable excipient, preferably 5% mannitol (w/v), for infusion.

Example 5

Synthesis of Compound B; 2-[(1E)-1-(2-{6-methyl-5H-[1,2,4]triazino[5,6-b]indole-3-yl}hydrazin-1-ylidene)propyl]pyridine 1-(pyridin-2-yl)propan-1-one (35 mg, 0.26 mmol) was dissolved in a water-acetic acid mixture (20:1, 10 mL) then 3-hydrazinyl-6-methyl-5H-[1,2,4]triazino[5,6-b]indole (50 mg, 0.23 mmol) was added. The reaction mixture was stirred for 2 hours at 50° C. After evaporating the solvents, a dark green solid was obtained (70 mg). LC shows pure product with an isomer ratio of 95:5.

Example 6

Synthesis of Compound C; 2-(3,3-dimethyl-N-{6-methyl-5H-[1,2,4]triazino[5,6-b]indole-3-yl}butanehydrazonoyl)pyridine 3,3-dimethyl-1-(pyridin-2-yl)butan-1-one (46 mg, 0.26 mmol) was measured in a water-acetic acid mixture (20:1, 10 mL) then 3-hydrazinyl-6-methyl-5H-[1,2,4]triazino[5,6-b]indole (48 mg, 0.23 mmol) was added. The reaction mixture was stirred overnight at 50° C. After evaporating the solvents, a greenish yellow solid was obtained (78 mg). LC showed pure product with an isomer ratio of 92:8.

Example 7

The conversion of compound B1 to its di-hydrochloride (B2) was prepared by the following procedure:

2-[(1E)-1-(2-{6-methyl-5H-[1,2,4]triazino[5,6-b]indole-3-yl}hydrazin-1-ylidene)propyl]pyridine (30 mg, 0.09 mmol) was suspended in methanol (0.6 mL), then HCl in ethanol (1.04 equiv. 1.25 M, 75 µL) was added dropwise. After all the solid was dissolved, more HCl in ethanol (2.08 equiv. 1.25 M, 150 µL) and ethanol (0.6 mL) was added. A light brown precipitate appeared. The suspension was kept at −10° C. for 3 hours, then the solid was filtered, washed with cold ethanol and dried. The product was a bright yellow solid (10 mg). LC shows only one isomer, the minor isomer is not detected after converting the product to its HCl salt.

Example 8

The conversion of compound C1 to its di-hydrochloride C2 was prepared by the following procedure: 2-[(1E)-1-(2-{6-methyl-5H-[1,2,4]triazino[5,6-b]indol-3-yl}hydrazin-1-ylidene)propyl]-pyridine (30 mg, 0.09 mmol) was suspended in methanol (0.6 mL), then HCl in ethanol (1.04 equiv. 1.25 M, 75 µL) was added dropwise. After all the solid was dissolved, more HCl in ethanol (2.08 equiv. 1.25 M, 150 µL) and ethanol (0.6 mL) was added. The product did not precipitate immediately, only after the suspension was kept at −10° C. for 3 hours. The solid was filtered, washed with cold ethanol and dried. The product was a bright yellow solid (20 mg). LC shows only one isomer (E), the minor isomer (Z) is not detected after converting the product to its HCl salt.

Characterization

Single crystal X-ray showed that the E-isomer is predominant in the solid state.

Figure 2B:
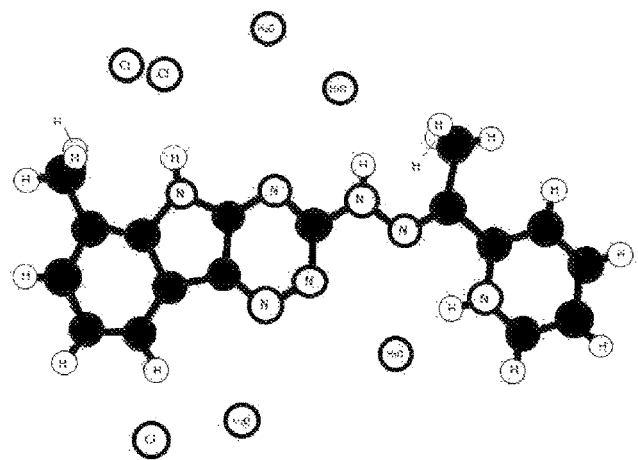
FIG. 2b illustrates the E-isomer structure of compound A1 confirmed by X-ray chromatography.

Single Crystal X-ray was performed at SARomics Biostructures AB, Sweden. Crystals of compound A1 measuring about 100×30 µm were picked up in standard cryo loops of the kind normally used for protein crystals, immersed in paraffin oil and flash-cooled in liquid nitrogen. Data were collected at 100 K at station I911-3 of MAX-lab ($\lambda$=0.9198 Å), equipped with a 225 mm mar CCD detector. The beam size was 50×50 µm. The x-ray results confirm that compound A1 is the E-hydrazone isomer. The predicted structure is shown in FIG. 2b, where N stands for nitrogen atoms, H for hydrogen atoms, CL for chloride atoms, and H$_2$O for water molecules.

All testing was performed using reference standard, and, all analyses are in agreement with the proposed structure.

Conclusion

A water content of 4-7% in the starting material of compound A was tolerable, even though the product compound A2 readily hydrolyses in aqueous solvents.

There was no trace of isomer in the mother liquor, showing that the applied precipitation condition converts the Z-isomer to the target E-isomer. Preferably, the salt formation should be performed within hours since the product is acid sensitive.

The composition development work was initiated with the aqueous solvent stability testing and excipient evaluation discussed above. Based on these results, the composition development continued by optimising the composition (i.e. drug substance—the ethanol co-crystal precipitate-concentration and type and quantity of excipient) with regards to the effect on impurity formation and solubility of the drug product (i.e., the di-hydrochloride salt, for example compound A2). As a result of the optimisation the amount of the free base (compound A) per vial was increased from 100 to 160 mg.

Example 9

Cytotoxic Activity

Cytotoxic activity expressed as survival Index, (IC50), by compound A is shown in various cell lines (FIG. 3) and primary cultures of human tumors (Table 5). The Fluorometric Microculture Cytotoxicity Assay (FMCA), (Lindhagen et al., 2008), was used for measurement of the cytotoxic effect of the compounds in various cell lines and primary cultures of human tumors. Cells were seeded in the drug-prepared 384-well plates using the pipetting robot Precision 2000 (Bio-Tek Instruments Inc., Winooski, Vt.). The plates were incubated for 72 h and then transferred to an integrated HTS SAGIAN Core System consisting of an ORCA robot (Beckman Coulter) with CO$_2$ incubator (Cytomat 2C, Kendro, Sollentuna, Sweden), dispenser module (Multidrop 384, Titertek, Huntsville, Ala.), washer module (ELx 405, Bio-Tek Instruments Inc), de-lidding station, plate hotels, barcode reader (Beckman Coulter), liquid handler (Biomek 2000, Beckman Coulter) and a multipurpose reader (FLUOstar Optima, BMG Labtech GmbH, Offenburg, Germany) for automated FMCA.

Figure 3:
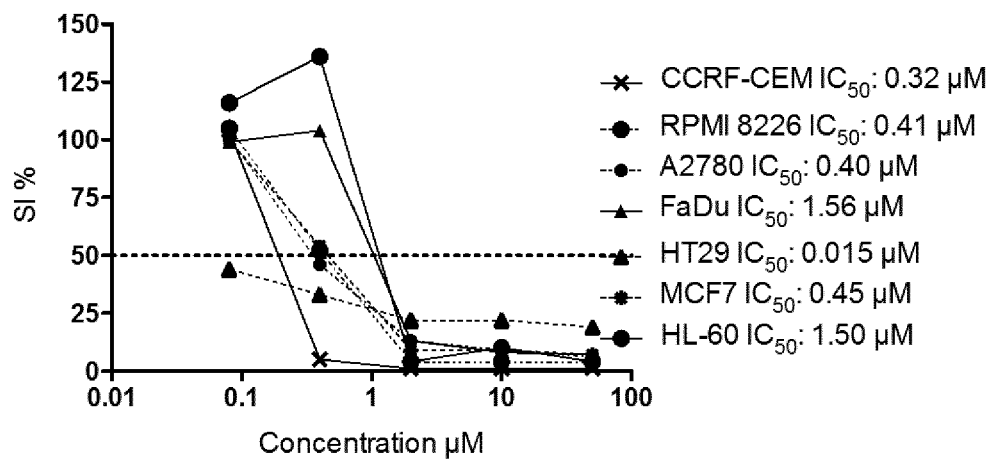
FIG. 3 show dose-response curves for compound A in various cell lines.

Different cell lines (e.g. CCRF-CEM T-cell leukemia, RPMI-8226 multiple myeloma, A2780 ovarian carcinoma, FaDu head & neck cancer (squamous cell carcinoma tumor), HT29 colorectal cancer, MCF7 breast cancer, and HL-60 leukemia cells) as well as panels of primary human tumor cell cultures (Table 5) were analyzed (colon, gastric, kidney, appendix, small bowel and pancreas cancer, as well as pseudomyxoma peritonei). Results show broad anti-cancer activity of compound A, as exemplified in the effect-concentration graph (FIG. 3).

Example 10

The inventors also set out to characterize activity of the compounds A, B and C in cell lines representing cancer of different origin. The specific assays used and the conclusions from the mechanistic evaluation have previously been described in detail (Zhang et al. 2014). Compounds A, B and C (See FIG. 4) were evaluated for cytotoxicity expressed as survival index (SI) in six human tumor cell lines using the cell based fluorometric micro culture cytotoxicity assay (FMCA) as previously described in detail (Lindhagen et al, 2008). The method is based on measurement of fluorescent fluorescein, generated from hydrolysis of FDA by viable cells with intact plasma membrane. The fluorescence is proportional to the number of intact viable cells.

Material and Methods

Cell Culture

The cell lines were cultivated in the respective cell medium recommended by the provider. The medium was supplemented with 10% heat-inactivated fetal bovine serum, 2 mmol/L L-glutamine, 100 µg/mL streptomycin and 100 U/mL penicillin (all from Sigma-Aldrich). The cell line was cultured at 37° C. in a humidified atmosphere containing 5% CO$_2$.

Measurement of Cytotoxic Activity

FMCA analysis in brief, 2500 cells per well were seeded into 384-well microplates and incubated over night before treatment with compounds. Compounds were added using acoustic liquid transfer (Echo 550, LabCyte). The plates were incubated at 37° C. for 72 h, and then washed and FDA was added to the wells followed by 50 min of incubation at 37° C. The fluorescence, which is proportional to the number of living cells in each well, was measured at 485/520 nm in a Fluoroskan instrument (Labsystems, GMI, Ramsey, Minn.). Cell survival is presented as Survival Index (SI), defined as the fluorescence value in the compound-treated wells analysed as percentage of the value in the control wells, with blank values subtracted. Quality criteria included a signal/blank ratio >10 and a coefficient of variation (CV) in control and blank wells <30%. Graph Pad Prism (San Diego, Calif., USA). All experiments were performed twice, and each concentration was evaluated in quadruplicates in each experiment. The compounds (A, B and C) were diluted DMSO, 5 mM.

TABLE 5

IC$_{50}$ in panels of different primary human tumor cell cultures

| Disease | No of patients analyzed | IC$_{50}$ µM |
| --- | --- | --- |
| PMP* | 50 | 9.4 |
| Colorectal** | 25 | 11 |
| Gastric | 9 | 6.9 |
| Renal | 13 | 164 |
| Mesothelioma | 7 | 12 |
| Appendix | 4 | 21 |
| Small bowel | 1 | 5.4 |
| Ovarian | 30 | 5.7 |
| Pancreas | 1 | 6.0 |

Figure 4:
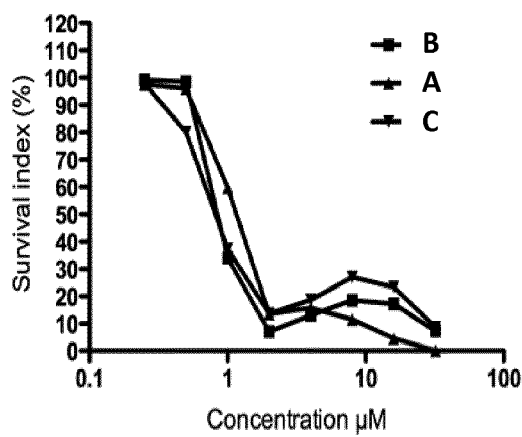
FIGS. 4a-d show dose-response curves for compound A, B and C in HCT116-cells (A), and in HepG2-cells, RKO-cells, HeLa-cells, CEM-cells and THP-1 cells for compound A (b), for compound B (c) and for compound C (d).

*Pseudomyxoma Peritonei,
**Colorectal cancer, surgical specimens obtained from maximal cytoreductive surgery and peritinectomies Results and Discussion The tested compounds (A, B and C) showed strong activity on a wide range of cancer cell lines, see Table 6 and FIG. 4. The cell lines were selected to cover a wide range of cancer types, representing both haematological and solid tumors (Table 6).

From these results, it is clearly shown that compounds A, B and C are effective against several different tumor cell lines including colon carcinoma, cervix adenocarcinoma, hepatocellular carcinoma, acute lymphoblastic leukemia and acute monocytic leukemia.

From the results presented here, it is clearly shown that compounds A, B and C are effective against several different tumor cell lines including colon carcinoma, cervix adenocarcinoma, hepatocellular carcinoma, acute lymphoblastic leukemia and acute monocytic leukemia.

TABLE 6

IC$_{50}$ for compounds A, B and C in six human tumor cell lines.

| Cell line | Origin | IC$_{50}$ Compound A | IC$_{50}$ Compound B | IC$_{50}$ Compound C |
| --- | --- | --- | --- | --- |
| HCT116 | Colon carcinoma | ≈1 µM | ≈1 µM | ≈1 µM |
| RKO | Colon carcinoma | <250 nM | <250 nM | <250 nM |
| HeLa | Cervix Adenocarcinoma | ≈20 µM | ≈20 µM | ≈10 µM |
| HepG2 | Hepatocellular Carcinoma | <250 nM | <250 nM | <250 nM |
| CCRF-CEM | Acute lymphoblastic leukemia | <250 nM | <250 nM | <250 nM |
| THP-1 | Acute Monocytic Leukemia | <250 nM | <250 nM | <250 nM |

Although particular embodiments have been discussed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

REFERENCES

Eshba et al. *Synthesis of some substituted-1,2,4-triazino [5,6-b]indole derivatives as potential antiviral and anticancer agents*. Pharmazie Vol. 42, No. 10, 1987; 664-666.

Lindhagen E, Nygren P, Larsson R (2008) The fluorometric microculture cytotoxicity assay. Nature Protocols 3: 1364-1369.

Kgokong J L, Smith P P, Matsabisa G M (2005) Bioorg Med Chem. 13(8):2935-42).

Zhang X et al. (2014) Induction of mitochondrial dysfunction as a strategy for targeting tumor cells in metabolically compromised microenvironments. Nature communications 5:3295.

The invention claimed is:

1. A pharmaceutical composition for use in treating cancer selected from the group of colon carcinoma, colorectal, cervix adenocarcinoma, hepatocellular carcinoma, acute lymphoblastic leukemia, acute monocytic leukemia, leukemia, multiple myeloma, mesothelioma, ovarian carcinoma, breast cancer, FaDu, appendix, small bowel, PMP (pseudomyxoma peritonei), gastric, and renal cancer, said composition comprising a di-hydrochloride salt in crystalline form of a pharmaceutically active compound of general formula 1, or a pharmaceutically acceptable salt thereof, a lyophilisate thereof, a precipitate thereof or mixtures thereof

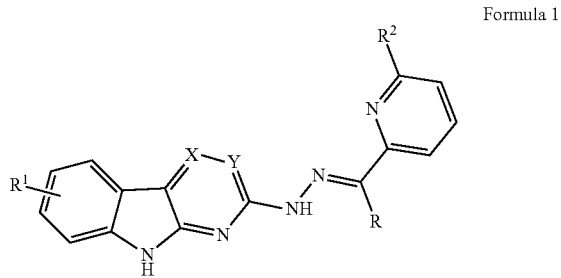

Formula 1 wherein,
R is H or methyl or methylene substituted by $C_1$-$C_4$ straight or branched alkyl,
$R^1$ is selected from the group consisting of $C_1$-$C_4$ straight or branched alkyl, methoxy, methoxy substituted with from one to three fluorine, bromide, halogen;
$R^2$ is H or $C_1$-$C_4$ straight or branched alkyl;
X is CH or N;
Y is CH or N, and wherein at least 95% by weight (w/w) of the pharmacologically active compound, or pharmaceutically acceptable salt thereof is in the form of the E-isomer, wherein the pharmaceutical composition has a pH of 0.5-4 and is stable for at least 12 months at room temperature when in the form of the lyophilisate and/or precipitate.

2. The pharmaceutical composition according to claim 1, further comprising a pharmaceutically acceptable excipient in the concentration of 0.1-10% (w/v).

3. A process for preparing the pharmaceutical composition according to claim 1 comprising the following steps:
  i. providing a solution of a compound of general formula 1 as a free base,
  ii. reacting the solution with hydrochloric acid in ethanol in sufficient amounts to form a compound of general formula 1 to a di-hydrochloride salt, wherein the di-hydrochloride salt precipitates spontaneously;
  iii. stripping the precipitate comprising the di-hydrochloride salt obtained in step (ii) of solvent,
  iv. dissolving the di-hydrochloride salt of step (iii) in an aqueous solvent, optionally comprising a pharmaceutically acceptable excipient, and
  v. freeze drying the mixture thereby obtaining a lyophilized powder or cake.

4. A precipitate comprising a compound of general formula 1b,

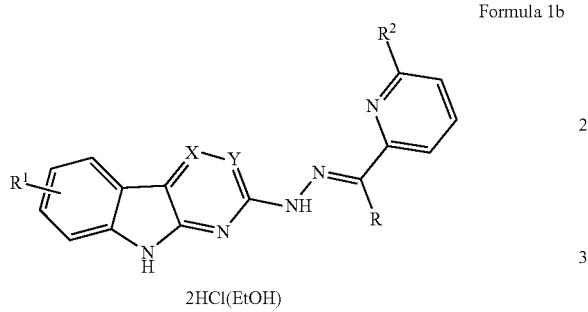

Formula 1b

2HCl(EtOH)

wherein R is H or methyl or methylene substituted by $C_1$-$C_4$ straight or branched alkyl,
$R^1$ is selected from the group consisting of $C_1$-$C_4$ straight or branched alkyl, methoxy, methoxy substituted with from one to three fluorine, bromide, halogen;
$R^2$ is H or $C_1$-$C_4$ straight or branched alkyl;
X is CH or N;
Y is CH or N, and wherein at least 95% by weight (w/w) of compound 1b is in the form of the E-isomer.

5. A process for preparing the precipitate according to claim 4, comprising the following steps:
  providing a solution of a compound of general formula 1 as a free base,

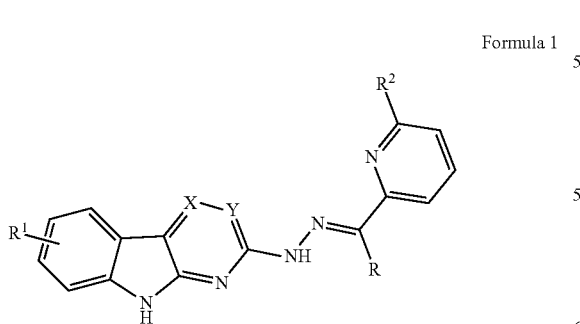

Formula 1 wherein,
R is H or methyl or methylene substituted by $C_1$-$C_4$ straight or branched alkyl,
$R^1$ is selected from the group consisting of $C_1$-$C_4$ straight or branched alkyl, methoxy, methoxy substituted with from one to three fluorine, bromide, halogen;

$R^2$ is H or $C_1$-$C_4$ straight or branched alkyl;
X is CH or N;
Y is CH or N,
and
reacting the solution with hydrochloric acid in ethanol in sufficient amounts to form a compound of general formula 1 to a di-hydrochloride salt, wherein the di-hydrochloride salt precipitates spontaneously; and optionally stripping the precipitate comprising the di-hydrochloride salt obtained in step (ii) of solvent.

6. The precipitate according to claim 4 wherein residual ethanol is in the range of 2-20% by weight of the di-hydrochloride salt precipitate.

7. A lyophilisate comprising a compound of general formula 1a,

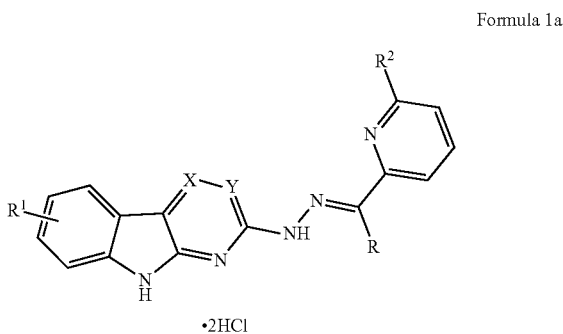

Formula 1a

·2HCl wherein R is H or methyl or methylene substituted by $C_1$-$C_4$ straight or branched alkyl,
$R^1$ is selected from the group consisting of $C_1$-$C_4$ straight or branched alkyl, methoxy, methoxy substituted with from one to three fluorine, bromide, halogen;
$R^2$ is H or $C_1$-$C_4$ straight or branched alkyl;
X is CH or N;
Y is CH or N, and wherein at least 95% by weight (w/w) of compound 1a is in the form of the E-isomer.

8. A process for preparing the lyophilisate according to claim 7 comprising the following steps:
  i. dissolving a di-hydrochloride salt precipitate of formula 1b,

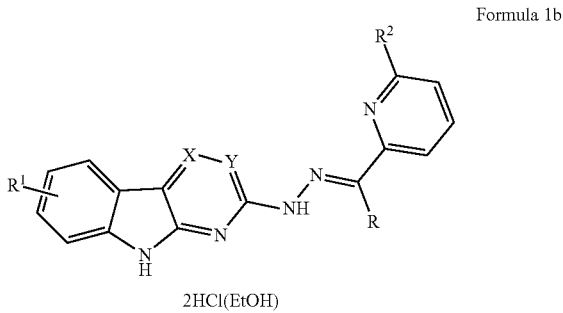

Formula 1b

2HCl(EtOH)

in an aqueous solvent, optionally comprising a pharmaceutically acceptable excipient,
and
  ii. freeze drying the mixture thereby obtaining a lyophilized powder or cake.

9. The precipitate according to claim 4 and a lyophilisate comprising a compound of general formula 1a,

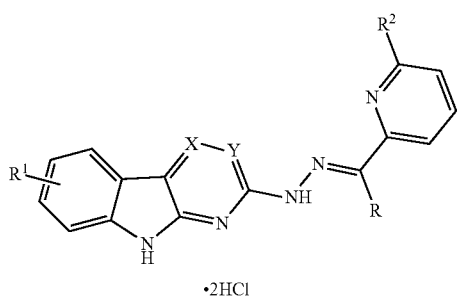

Formula 1a

•2HCl wherein R is H or methyl or methylene substituted by $C_1$-$C_4$ straight or branched alkyl, $R^1$ is selected from the group consisting of $C_1$-$C_4$ straight or branched alkyl, methoxy, methoxy substituted with from one to three fluorine, bromide, halogen;

$R^2$ is H or $C_1$-$C_4$ straight or branched alkyl;

X is CH or N;

Y is CH or N, and wherein at least 95% by weight (w/w) of compound 1 a is in the form of the E-isomer for use in a pharmaceutical composition.

10. A pharmaceutical formulation suitable for infusion prepared by reconstituting the pharmaceutical composition, or a pharmaceutically acceptable salt thereof, a lyophilisate thereof, a precipitate thereof or mixtures thereof according to claim 1 in an aqueous solvent at a final concentration in the range of 0.5-30 mg/ml.

11. A method for treating cancer in a subject selected from the group of colon carcinoma, colorectal, cervix adenocarcinoma, hepatocellular carcinoma, acute lymphoblastic leukemia, acute monocytic leukemia, leukemia, multiple myeloma, mesothelioma, ovarian carcinoma, breast cancer, FaDu, appendix, small bowel, PMP (pseudomyxoma peritonei), gastric, and renal cancer, in which an effective amount of a pharmaceutical composition comprising the compound, or a pharmaceutically acceptable salt thereof, a lyophilisate thereof, a precipitate thereof or mixtures thereof according to claim 1 is administered by infusion or injection to a subject in need thereof.

12. A method for treating cancer in a subject selected from the group of colon carcinoma, colorectal, cervix adenocarcinoma, hepatocellular carcinoma, acute lymphoblastic leukemia, acute monocytic leukemia, leukemia, multiple myeloma, mesothelioma, ovarian carcinoma, breast cancer, FaDu, appendix, small bowel, PMP (pseudomyxoma peritonei), gastric, and renal cancer, in which an effective amount of a pharmaceutical composition comprising the compound, or a pharmaceutically acceptable salt thereof, a lyophilisate thereof, a precipitate thereof or mixtures thereof according to claim 1 is administered to a subject in need of such treatment.

13. The method for the treatment of cancer according to claim 12 in combination with another anticancer treatment.

14. The method for treating cancer according to claim 12 wherein the effective dose is in the range of 0.01-10 mg/kg body weight.

15. The pharmaceutical formulation according to claim 10, further comprising a pharmaceutically acceptable excipient in the concentration of 0.1-10% (w/v).

* * * * *